United States Patent
Joseph et al.

(10) Patent No.: US 9,067,920 B2
(45) Date of Patent: Jun. 30, 2015

(54) COMPOUNDS USEFUL FOR INHIBITING CHK1

(75) Inventors: Sajan Joseph, Carmel, IN (US); Susanta Samajdar, Karnataka (IN)

(73) Assignee: Eli Lilly and Company, Indianapolis, IN (US)

( * ) Notice: Subject to any disclaimer, the term of this patent is extended or adjusted under 35 U.S.C. 154(b) by 113 days.

(21) Appl. No.: 13/877,923

(22) PCT Filed: Nov. 1, 2011

(86) PCT No.: PCT/US2011/058692
§ 371 (c)(1),
(2), (4) Date: Apr. 5, 2013

(87) PCT Pub. No.: WO2012/064548
PCT Pub. Date: May 18, 2012

(65) Prior Publication Data
US 2013/0190262 A1  Jul. 25, 2013

Related U.S. Application Data

(60) Provisional application No. 61/411,137, filed on Nov. 8, 2010.

(51) Int. Cl.
C07D 401/14 (2006.01)
A61K 31/497 (2006.01)
A61K 31/704 (2006.01)
A61K 31/7068 (2006.01)
C07C 53/10 (2006.01)
C07C 55/07 (2006.01)
C07C 55/10 (2006.01)
C07C 309/04 (2006.01)

(52) U.S. Cl.
CPC ............ *C07D 401/14* (2013.01); *A61K 31/497* (2013.01); *A61K 31/704* (2013.01); *A61K 31/7068* (2013.01); *C07C 53/10* (2013.01); *C07C 55/07* (2013.01); *C07C 55/10* (2013.01); *C07C 309/04* (2013.01)

(58) Field of Classification Search
CPC .... C07D 401/14; C07C 309/04; C07C 53/10; C07C 55/07; C07C 55/10; A61K 31/497; A61K 31/704; A61K 31/7068
USPC .......................... 514/34, 255.05, 49; 544/405
See application file for complete search history.

(56) References Cited

FOREIGN PATENT DOCUMENTS

| WO | WO 2005/009435 A1 | 2/2005 |
| WO | WO 2005/121121 A2 | 12/2005 |
| WO | WO 2008/117050 A1 | 10/2008 |

OTHER PUBLICATIONS

Zenvirt et al. Status of p53 in human cancer ceUs does not predict efficacy of CHK1 kinase inhibitors combined with chemotherapeutic agents. Oncogene 29:6149-6159, 2010.*
Garrett et al. Anticancer therapy with checkpoint inhibitors: what, where and when? Trend Pharmacol Sci 32:308-316, 2011.*
McNeely et al. CHEK again: Revisiting the development of CHK1 inhibitors for cancer therapy. Pharmacol THerap 142:1-10, 2014.*

* cited by examiner

*Primary Examiner* — Brandon Fetterolf
*Assistant Examiner* — Yih-Horng Shiao
(74) *Attorney, Agent, or Firm* — Danica Hostettler

(57) ABSTRACT

The present invention provides an aminopyrazole compound, or a pharmaceutically acceptable salt thereof, that inhibits Chk1 and is useful in the treatment of cancer.

10 Claims, No Drawings

COMPOUNDS USEFUL FOR INHIBITING CHK1

This application is a national phase application, under 35 U.S.C. §371, for PCT/US2011/058692, filed Nov. 1, 2011, which claims priority to U.S. Provisional Application No. 61/411,137, filed Nov. 8, 2010.

The present invention relates to an aminopyrazole compound, or a pharmaceutically acceptable salt thereof, that inhibits Chk1 and is useful for treating cancers characterized by defects in deoxyribonucleic acid (DNA) replication, chromosome segregation, and/or cell division.

Chk1 is a protein kinase that lies downstream from Atm and/or Atr in the DNA damage checkpoint signal transduction pathway. In mammalian cells, Chk1 is phosphorylated in response to agents that cause DNA damage including ionizing radiation (IR) ultraviolet (UV) light, and hydroxyurea. This phosphorylation which activates Chk1 in mammalian cells is dependent on Atr. Chk1 plays a role in the Atr dependent DNA damage checkpoint leading to arrest in S phase and at G2M. Chk1 phosphorylates and inactivates Cdc25A, the dual-specificity phosphatase that normally dephosphorylates cyclin E/Cdk2, halting progression through S-phase. Chk1 also phosphorylates and inactivates Cdc25C, the dual specificity phosphatase that dehosphorylates cyclin B/Cdc2 (also known as Cdk1) arresting cell cycle progression at the boundary of G2 and mitosis (Funari et al., *Science*, 277:1495-7, 1997). In both cases, regulation of Cdk activity induces a cell cycle arrest to prevent cells from entering mitosis in the presence of DNA damage or unreplicated DNA.

Various inhibitors of Chk1 have been reported. In addition, WO 2005/121121 discloses certain aminopyrazole compounds asserted to be modulators of glucose metabolism.

However, there is still a need for Chk1 inhibitors that are potent inhibitors of the cell cycle checkpoints that can act effectively as potentiators of DNA damaging agents. The present invention provides compounds that are potent inhibitors of Chk1, which may be beneficial for the treatment of cancer. The compounds potently abrogate a Chk1 mediated cell cycle arrest induced by treatment with DNA damaging agents in tissue culture and in vivo. Additionally, the compounds of the present invention provide inhibition of Chk2, which may be beneficial for the treatment of cancer. Furthermore, the compounds of the present invention inhibit cell proliferation of cancer cells by a mechanism dependent on Chk1 inhibition. Such new compounds could address the need for safe and effective treatments of cancer.

The present invention provides a compound which is (R)-[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof. Preferred embodiments are (R)-[5-(2-methoxy-6-methyl-pyridin-3-yl)-2H-pyrazol-3-yl]-[6-(piperidin-3-yloxy)-pyrazin-2-yl]-amine, (R)-[5-(2-methoxy-6-methyl-pyridin-3-yl)-2H-pyrazol-3-yl]-[6-(piperidin-3-yloxy)-pyrazin-2-yl]-amine methane sulfonic acid salt, (R)[5-(2-methoxy-6-methyl-pyridin-3-yl)-2H-pyrazol-3-yl]-[6-(piperidin-3-yloxy)-pyrazin-2-yl]-amine acetic acid salt, (R)-[5-(2-methoxy-6-methyl-pyridin-3-yl)-2H-pyrazol-3-yl]-[6-(piperidin-3-yloxy)-pyrazin-2-yl]-amine hemioxalate salt, and (R)-[5-(2-methoxy-6-methyl-pyridin-3-yl)-2H-pyrazol-3-yl]-[6-(piperidin-3-yloxy)-pyrazin-2-yl]-amine hemisuccinate salt.

As a particular embodiment, the present invention provides the compound which is (R)[5-(2-methoxy-6-methyl-pyridin-3-yl)-2H-pyrazol-3-yl]-[6-(piperidin-3-yloxy)-pyrazin-2-yl]-amine.

The present invention provides the methane sulfonic acid, acetic acid, hemioxalate, and hemisuccinate salts of (R)-[5-(2-methoxy-6-methyl-pyridin-3-yl)-2H-pyrazol-3-yl]-[6-(piperidin-3-yloxy)-pyrazin-2-yl]-amine.

Another embodiment is a hydrate of (R)-[5-(2-methoxy-6-methyl-pyridin-3-yl)-2H-pyrazol-3-yl]-[6-(piperidin-3-yloxy)-pyrazin-2-yl]-amine.

The present invention provides (R)[5-(2-methoxy-6-methyl-pyridin-3-yl)-2H-pyrazol-3-yl]-[6-(piperidin-3-yloxy)-pyrazin-2-yl]-amine hydrate in crystalline form.

The present invention also provides (R)-[5-(2-methoxy-6-methyl-pyridin-3-yl)-2H-pyrazol-3-yl]-[6-(piperidin-3-yloxy)-pyrazin-2-yl]-amine hydrate in crystalline form characterized by a X-ray powder diffraction pattern having peaks at $2\theta \pm 0.2$ at 5.17 in combination with one or more of the peaks selected from the group consisting of 15.73, 17.71 and 20.12.

The present invention provides a pharmaceutical composition comprising (R)-[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof, and a pharmaceutically acceptable carrier, diluent, or excipient.

The present invention provides a pharmaceutical composition comprising (R)-[5-(2-methoxy-6-methyl-pyridin-3-yl-2H-pyrazol-3-yl]-[6-(piperidin-3-yloxy)-pyrazin-2-yl]-amine, or a pharmaceutically acceptable salt thereof, together with a pharmaceutically acceptable carrier, diluent, or excipient and optionally other therapeutic ingredients.

The present invention provides a method of treating cancer, comprising administering to a patient in need thereof an effective amount of (R)-[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof. In addition, the present invention also provides a method of treating cancer, comprising administering to a patient in need thereof an effective amount of (R)-[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof, and ionizing radiation. Furthermore, the present invention provides a method of treating cancer, comprising administering to a patient in need thereof an effective amount of (R)-[5-(2-meth oxy-6-methyl-pyridin-3-yl)-2H-pyrazol-3-yl]-[6-(piperidin-3-yloxy)-pyrazin-2-yl]-amine, or a pharmaceutically acceptable salt thereof, and one or more chemotherapy agents.

The present invention provides the use of (R)-[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof, for the manufacture of a medicament for the treatment of cancer. In addition, the present invention also provides the use of (R)[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof, for the manufacture of a medicament for the treatment of cancer wherein said treatment comprises combination therapy with ionizing radiation. Furthermore, the present invention provides the use of (R)[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof, for the manufacture of a medicament for the treatment of cancer by combination therapy wherein said combination therapy treatment comprises administration of said medicament and administration of one or more chemotherapy agents to the same patient.

The present invention provides (R)-[5-(2-methoxy-6-methyl-pyridin-3)-2H-pyrazol-3-yl]-[6-(piperidin-3-yloxy)-pyrazin-2-yl]-amine, or a pharmaceutically acceptable salt thereof, for use in therapy. In addition, the present invention also provides (R)-[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof, and ionizing radiation for use in therapy. Furthermore, the present invention provides (R)-[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof, and one or more chemotherapy agents for use in therapy.

The present invention provides (R)-[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof for use in the treatment of cancer. In addition, the present invention also provides (R)[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof, and ionizing radiation for use in the treatment of cancer. Furthermore, the present invention provides (R)-[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof, and one or more chemotherapy agents for use in the treatment of cancer.

The present invention provides use of (R)-[5-(2-methoxy-6-methyl-pyridin-3-yl) 2H-pyrazol-3-yl]-[6-(piperidin-3-yloxy)-pyrazin-2-yl]-amine, or a pharmaceutically acceptable salt thereof, for the manufacture of a medicament for the treatment of cancer, wherein the medicament is to be administered simultaneously, separately, or sequentially with ionizing radiation.

The present invention provides use of (R)-[5-(2-methoxy-6-methyl-pyridin-3-yl-2H-pyrazol-3-yl]-[6-(piperidin-3-yloxy)-pyrazin-2-yl]-amine, or a pharmaceutically acceptable salt thereof, for the manufacture of a medicament for the treatment of cancer, wherein the medicament also comprises one or more chemotherapy agents or is to be administered simultaneously, separately, or sequentially with one or more chemotherapy agents.

The present invention provides (R)-[5-(2-methoxy-6-methyl-pyridin-3-yl-2H-pyrazol-3-yl]-[6-(piperidin-3-yloxy)-pyrazin-2-yl]-amine, or a pharmaceutically acceptable salt thereof, for use in simultaneous, separate, or sequential combination with ionizing radiation in the treatment of cancer.

The present invention provides (R)-[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof, for use in simultaneous, separate, or sequential combination with one or more chemotherapy agents in the treatment of cancer.

Furthermore, the present invention provides preferred embodiments of the methods and uses as described herein, in which the one or more chemotherapy agents is selected from the group consisting of 5-fluorouracil, hydroxyurea, gemcitabine, methotrexate, pemetrexed, doxorubicin, etoposide, cisplatin, and taxol. Additionally, the present invention provides more preferred embodiments of the methods and uses as described herein, in which two chemotherapy agents are selected, from the group consisting of 5-fluorouracil, hydroxyurea, gemcitabine, methotrexate, pemetrexed, doxorubicin, etoposide, cisplatin, and taxol. Also, the present invention provides even more preferred embodiments of the methods and uses as described herein, in which the chemotherapy agent is selected from the group consisting of 5-fluorouracil, hydroxyurea, gemcitabine, methotrexate, pemetrexed, doxorubicin, etoposide, cisplatin, and taxol. Preferred embodiments of the methods and uses described herein are cancers selected from the group consisting of bladder cancer, colon cancer, gastric cancer, liver cancer lung cancer, mammary cancer, melanoma, ovarian cancer, pancreatic cancer, mesothelioma, renal cancer, and uterine cancer.

As used above, and throughout the description of the invention, the following terms, unless otherwise indicated, shall be understood to have the following meanings:

"Pharmaceutically acceptable salt" or "pharmaceutically acceptable salts" refers to the relatively non-toxic, inorganic and organic salts of compounds of the present invention.

The compounds of the present invention are capable of reaction, for example, with a number of inorganic and organic acids to form pharmaceutically acceptable salts. Such pharmaceutically acceptable salts and common methodology for preparing them are well known in the art. See, e.g., P. Stahl, et al., Handbook of Pharmaceutical Salts: Properties, Selection, and Use, (VCHA/Wiley-Val, 2002); S. M. Berge, et al., "Pharmaceutical Salts", *Journal of Pharmaceutical Sciences*, Vol. 66, No. 1, January 1977.

The compounds of the present invention are preferably formulated as pharmaceutical compositions using one or more pharmaceutically acceptable carriers, diluents, or excipients and administered by a variety of routes, Preferably, such compositions are for oral, subcutaneous, or intravenous administration. Such pharmaceutical compositions and processes for preparing them are well known in the art. See, e.g., Remington: The Science and Practice of Pharmacy (A. Gennaro, et al., eds., 21st ed., Mack Publishing Co., 2005).

The terms "treatment," "treat," "treating," and the like, are meant to include slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed.

"Therapeutically effective amount" or "effective amount" means the amount of the compound, or pharmaceutically acceptable salt thereof, of the present invention or pharmaceutical composition containing a compound, or pharmaceutically acceptable salt thereof, of the present invention that will elicit the biological or medical response of or desired therapeutic effect on a tissue, system, animal, mammal, or human that is being sought by the researcher, veterinarian, medical doctor, or other clinician.

The amount of compound of the present invention actually administered will be determined by a physician under the relevant circumstances, including the condition to be treated, the chosen route of administration, the actual compound of the present invention administered, the age, weight, and response of the individual patient, and the severity of the patient's symptoms. Dosages per day normally fall within the range of about 0.1 to about 10 mg/kg of body weight. In some instances dosage levels below the lower limit of the aforesaid range may be more than adequate, while in other cases still larger doses may be employed.

The compounds of the present invention may be prepared by a variety of procedures known in the art, as well as those described in the Preparations and Examples below. The specific synthetic steps for each of the routes described may be combined in different ways to prepare the compounds of the present invention.

The reagents and starting materials are generally readily available to one of ordinary skill in the art. Others may be made by standard techniques of organic and heterocyclic chemistry, techniques which are analogous to the syntheses of known structurally similar compounds and the procedures described in the Preparations and Examples which follow, including any novel procedures. The following Preparations and Examples are provided to illustrate the invention in further detail and represent typical syntheses of the compounds. The names of the compounds of the present invention are generally provided by ISIS Draw 2.5 SP2 with Autonom add-in.

As used herein, the following terms have the meanings indicated: "BCA" refers to bicinchoninic acid; "BSA" refers to bovine serum albumin; "DMSO" refers to dimethylsulfoxide; "DPBS" refers to dibasic phosphate-buffered saline; "DTT" refers to dithiothreitol; "EtOAc" refers to ethyl acetate; "FBS" refers to fetal bovine serum; "HEPES" refers to N-2-hydroxyethylpiperazine-N'-2-ethanesulfonic acid; "MEM" refers to minimum essential medium; "MeOH" refers to methanol; "PBS" refers to phosphate-buffered saline; "PI" refers to propidium iodide; "RNAase" refers to ribonuclease A; "RPMI" refers to Roswell Park Memorial Institue; "TBST" refers to tris-buffered saline Tween-20; "THF" refers to tetrahydrofuran; "TR-FRET" refers to time resolved fluorescent energy transfer; "Tris" refers to tris(hydroxymethyl)aminomethane; "Triton-X" refers to 4-(1,1,3,3-tetramethylbutyl)phenyl-polyethylene glycol t-octylphenoxypolyethoxyethanol polyethylene glycol tert-octylphenyl ether; and "Tween-20" refers to polysorbate 20.

Preparation 1 tert-Butyl (R)-3-(6-chloropyrazin-2-yl)oxypiperidine-1-carboxylate

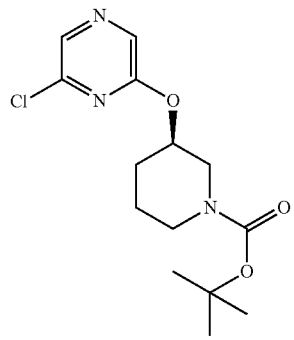 [SMILES: CC(C)(C)OC(=O)N1CCC[C@@H](Oc2cncc(Cl)n2)C1]

Sodium hydride (225.6 g, 5.64 mol) is dispersed into THF (3 L) and the temperature is lowered to 0-5° C. A solution of (R)-3-hydroxy-1-boc piperidine (891.6 g, 4.43 mol) in THF (3 L) is added over 1 h while maintaining the temperature between 0-5° C. The reaction is stirred for 1 h. 2,6-Dichloropyrazine (600 g, 4.03 mol) as a solution in THF (3 L) is added dropwise over 1.5 h maintaining the same temperature. The reaction is stirred for 2 h at 25-30° C., and then poured onto ice. The mixture is diluted with water and extracted with ethyl acetate. The extracts are dried over anhydrous sodium sulfate, filtered, and concentrated. The residual oil is triturated with 5% dichloromethane in hexane to give the product as a white solid. The solid is collected by filtration and dried, to give 1538 g crude material. The crude product is retriturated with 5% dichloromethane in hexanes to give a white solid in quantitative yield. ES/MS m/z 314.1 [M+H]$^+$.

Preparation 2

2-Methoxy-6-methyl-nicotinic acid methyl ester

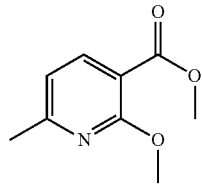

To a stirred solution of 2-chloro-6-methyl-nicotinic acid methyl ester (10.4 g, 56.52 mmol) in MeOH under nitrogen is added a solution of sodium (2.58 g, 113.04 mmol) in methanol (80.0 mL) (sodium metal is dissolved in methanol under a nitrogen atmosphere) at room temperature. The reaction mixture is refluxed overnight. The reaction is cooled to room temperature and the pH is adjusted to pH=7 with acetic acid. The reaction mixture is diluted with ethyl acetate (100 mL) and water (30 mL). The organic layer is separated and the aqueous layer is extracted with ethyl acetate (2×75 mL). The combined organic extracts are dried over Na$_2$SO$_4$, filtered, and concentrated to give crude product. Yield: 7.25 g (71%). $^1$H NMR (400 MHz, CDCl$_3$), δ8.066-8.047 (d, J=7.6 Hz, 1H), 6.782-6.764 (d, J=7.2 Hz, 1-1H), 4.029 (s, 3H), 3.879 (s, 3H), 2.483 (s, 3H); ES/MS m/z 182.2 [M+H]$^+$.

Preparation 3

5-(2-Methoxy-6-methyl-pyridin-3-yl)-2H-pyrazol-3-ylamine

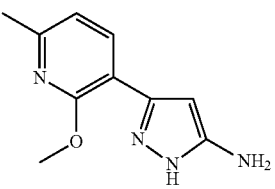

n-BuLi (1.2 M, 96.0 mL, 115.6 mmol) is added to a solution of acetonitrile (6.08 mL, 115.4 mmol) in THF (300 mL) at −78° C. and allowed to stir for 30 min at −78° C. 2-Methoxy-6-methyl-nicotinic acid methyl ester (20 g, 105.1 mmol) THE (200 mL) is added and stirred at −78° C. for another 30 min. The reaction mixture is quenched at −78° C. with water (500 mL) and washed with EtOAc (2×250 mL). The aqueous layer is separated and evaporated. This is co-distilled twice with toluene to obtain 3-(2-methoxy-6-methyl-pyridin-3-yl)-3-oxo-propionitrile. Yield=21.4 g (crude). ES/MS m/z 191.1 [M+H]$^+$.

A solution of 3-(2-methoxy-6-methyl-pyridin-3-yl)-3-oxo-propionitrile (21 g, 110.4 mmol) in ethanol (200 mL) is placed in a sealed tube, Hydrazine, hydrate (32.1 mL, 662.4 mmol) and acetic acid (21.0 mL) are added and the reaction heated at 100° C. for 2 h. The solvent is evaporated off and the reaction mixture is diluted with EtOAc (500 mL) and saturated sodium bicarbonate solution (100 mL). The organic layer is separated and the aqueous layer is extracted with EtOAc (2×250 mL). The combined organic extracts are dried over Na$_2$SO$_4$, filtered, and concentrated to give the crude product which is taken into the next step without any further purification. Yield=16.5 g (73%). ¹H NMR (400 MHz, DMSO-d₆) δ 11.50 (bs, 1H), 7.90 (d, J=7.6 Hz, 1H), 6.86 (d, J=7.6 Hz, 1H), 5.88 (s, 1H), 4.64 (s, 3H), 2.38 (s, 3H).

Preparation 4

5-Amino-3-(2-methoxy-6-methyl-pyridin-3-yl)-pyrazole-1-carboxylic acid tert-butyl ester

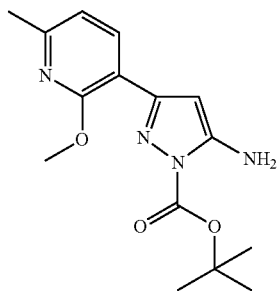 [SMILES: COc1nc(C)ccc1-c1cc(N)n(C(=O)OC(C)(C)C)n1]

A solution of 5-(2-methoxy-6-methyl-pyridin-3-yl)-2H-pyrazol-3-ylamine (16.0 g, 78.3 mmol) in THF (200 mL) is added slowly to a stirred suspension of NaH (60% in mineral oil, 14 g, 85.0 mmol) in THF (200 mL) at 0° C. After 15 min at 0° C., butyldicarbonate (19.8 mL, 86 mmol) is added slowly to the reaction mixture and stirred at 0° C. for 30 min. The reaction mixture is quenched with ice-water (approximately 250 mL) and the product is extracted into ethyl acetate (2×500 mL), The combined organic portions are washed with water and saturated NaCl solution (200 mL), dried over anhydrous Na₂SO₄, filtered, and concentrated under vacuum to afford crude material. This material is triturated with hexane twice to obtain 18.5 g (78%) of the title compound. ¹H NMR (400 MHz, DMSO-d₆) δ 8.05 (d, J=7.6 Hz, 1H), 6.90 (d, J=7.2 Hz, 1H), 6.28 (s, 2H), 5.85 (s, 1H), 3.90 (s, 3H), 1.56 (s, 9H).

Preparation 5

(R)-3-{6-[2-tert-Butoxycarbonyl-5-(2-methoxy-6-methyl-pyridin-3-yl)-2H-pyrazol-3-ylamino]-pyrazin-2-yloxy}-piperidine-1-carboxylic acid tert-butyl ester

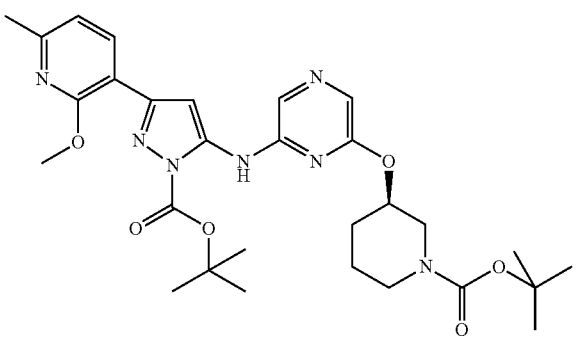 [SMILES: COc1nc(C)ccc1-c1cc(Nc2cncc(O[C@@H]3CCCN(C(=O)OC(C)(C)C)C3)n2)n(C(=O)OC(C)(C)C)n1]

A mixture of 5-amino-3-(2-methoxy-6-methyl-pyridin-3-yl)-pyrazole-1-carboxylic acid tert-butyl ester (50.0 g, 164.5 mmol), tert-butyl (R)-3-(6-chloropyrazin-2-yl)oxypiperidine-1-carboxylate (56.6 g, 180.9 mmol), 4,5-bis-diphenylphosphanyl-9,9-dimethyl-9H-xanthene (14.2 g, 24.6 mmol) and Cs₂CO₃ (85.5 g, 263 mmol) in 1,4-dioxane (1.4 L) is equally divided into two side by side round bottom flasks and both are purged with argon for 2 h. Pd(OAc)₂ (5.4 g, 24.6 mmol) is added (half to each vessel) and purging continues for 1 h. The reactions are then heated at 90-95° C. for 1 h. The reaction mixtures are cooled to room temperature, combined, and diluted with ethyl acetate (1 L). The mixture is then filtered through diatomaceous earth, washed with ethyl acetate and the filtrate is concentrated. The crude product is purified on silica gel with 15% EtOAc/hexane as eluent to provide 55 g (57% yield) of a white powder. The 55 g of purified product is combined with 15 g of similarly prepared and purified material (obtained, from 20 g of 5-amino-3-(2-methoxy-6-methyl-pyridin-3-yl)-pyrazole-1-carboxylic acid tert-butyl ester). The combined 70 g of material is dissolved in a 4:1 mixture of THF and methanol (1.4 L) and treated with QuadraSil™ AP (140 g) for 2 h. The reaction mixture is filtered through diatomaceous earth and washed with ethyl acetate (4×100 mL). The filtrate is again stirred with QuadraSil™ (140 g) for 2 h and filtered as above. The solvent is evaporated to give the title compound as a white solid. Yield=70 g (47%). ES/MS 582.5 [M+H]⁺.

EXAMPLE 1

(R)-[5-(2-Methoxy-6-methyl-pyridin-3-yl)-2H-pyrazol-3-yl]-[6-(piperidin-3-yloxy)-pyrazin-2-yl]-amine

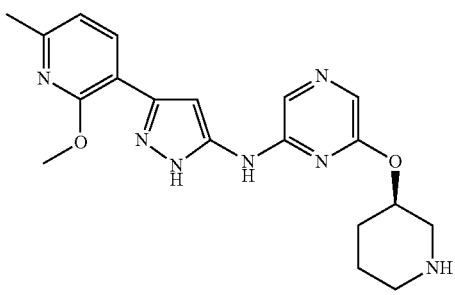 [SMILES: COc1nc(C)ccc1-c1cc(Nc2cncc(O[C@@H]3CCCNC3)n2)[nH]n1]

To a stirred solution of (R)-3-{6-[2-tert-butoxycarbonyl-5-(2-methoxy-6-methyl-pyridin-3-yl)-2H-pyrazol-3-ylamino]-pyrazin-2-yloxy}-piperidine-1-carboxylic acid tert-butyl ester (13.0 g, 22.3 mmol) in dichloromethane (150 mL) is added a solution of trifluoroacetic acid (12.4 mL, 167 mmol) dichloromethane (20 mL) over a period of 5 min at 0° C. The reaction is allowed to warm to room temperature and stirred for 3 h. The reaction is diluted with dichloromethane (1000 mL), followed by addition of saturated sodium bicarbonate solution (250 mL) and then stirred for 4 h. The organic portion is separated and dried over anhydrous sodium sulfate, filtered, and evaporated. The resulting material is crystallized from isopropanol to obtain the desired product. Yield=7.2 g (85%). ¹H NMR (400 MHz, DMSO-d₆) δ 12.40 (s, 1H), 9.71 (s, 1H), 8.02 (d, J=7.6 Hz, 1H), 7.97 (s, 1H), 7.46)(s, 1H), 6.93 (d, J=7.6 Hz, 1H), 6.91 (s, 1H), 4.94-4.86 (m, 1H), 3.97 (s, 3H), 3.20-3.13 (m, 1H), 2.83-2.75 (m, 1H), 2.57 (dd, J=12.0, 84 Hz, 1H), 2.53-2.45 (m obscured, 1H), 2.42 (s, 3H), 2.15-2.05 (m, 1H), 1.71-1.63 (m, 1H), 1.60-1.49 (m, 1H), 1.49-1.40 (m, 1H); ES/MS m/z 382.5 [M+H]⁺.

EXAMPLE 2

(R)-[5-(2-Methoxy-6-mcethyl-pyridin-3-yl)-2H-pyrazol-3-yl]-[6-(piperidin-3-yloxy)-pyrazin-2-yl]-amine methane sulfonic acid salt

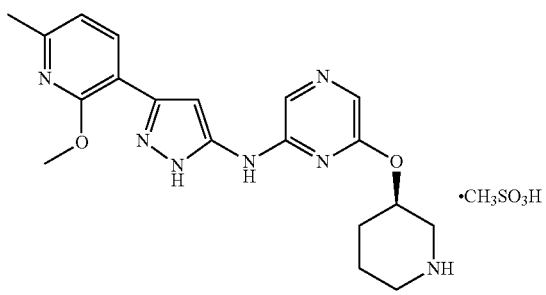

Methane sulfonic acid (0.247 g, 2.57 mmol) is added to a stirred solution of (R)-[5-(2-methoxy-6-methyl-pyridin-3-yl)-2H-pyrazol-3-yl]-[6-(piperidin-3-yloxy)-pyrazin-2-yl]-amine (0.982 g, 2.57 mmol) in dichloromethane (25 mL) at 0° C. The reaction is allowed to warm to room temperature and agitated for 45 min. The solvent is evaporated, and the resulting salt is washed with ether (10 mL) and pentane (10 mL), sequentially to obtain the desired product. Yield=1.139 g (92.6%), $^1$H NMR (400 MHz, DMSO-$d_6$), δ 12.5 (bs, 1H), 9.81 (s, 1H), 8.73 (bs, 1H)-8.54 (bs, 1H), 8.07 (s, 1H)-7.96 (d, J=7.6 Hz, 1H), 7.56 (s, 1H), 6.95 (d, J=7.6 Hz, 1H), 6.81 (s, 1H), 5.31-5.24 (m, 1H), 3.97 (s, 3H), 3.48-3.39 (m, 1H), 3.39-3.30 (m, 1H), 3.18-3.10 (m, 1H), 3.10-3.01 (m 1H), 2.43 (s, 3H), 2.32 (s, 3H), 2.03-1.85 (m, 3H), 1.73-1.65 (m, 1H); ES/MS m/z 382.4 [M+H]$^+$.

EXAMPLE 3

(R)-[5-(2-Methoxy-6-methyl-pyridin-3-yl)-2H-pyrazol-3-yl]-[6-(piperidin-3-yloxy)-pyrazin-2-yl]-amine acetic acid salt

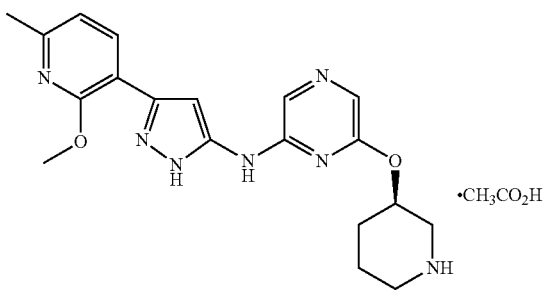

To a solution of (R)-[5-(2-methoxy-6-methyl-pyridin-3-yl)-2H-pyrazol-3-yl]-[6-(piperidin-3-yloxy)-pyrazin-2-yl]-amine (0.100 g, 0.26 mmol) in dichloromethane (10 mL) is added acetic acid (0.015 mL, 0.26 mmol) dissolved in dichloromethane (1 mL) at 0° C. The reaction mixture is stirred for 60 min at room temperature and then the solvent is evaporated to obtain a residue. The residue is triturated with diethyl ether (20 mL) followed by n-pentane (20 mL). The material is dried under high vacuum for 4 h to obtain the desired product. Yield=0.060 g (51.8%). $^1$H NMR (400 MHz, DMSO-$d_6$) δ 12.40 (bs, 1H), 9.70 (s, 1H), 8.02 (d, J=7.6 Hz, 1H), 7.98 (s, 1H), 7.46 (s, 1H), 6.94 (d, J=7.6 Hz, 1H), 6.90 (s, 1H), 4.97-4.38 (m, 1H), 3.98 (s, 3H), 3.20-3.13 (m, 1H), 2.83-2.74 (m, 1H), 2.66-2.56 (m, 1H), 2.42 (s, 3H), 2.14-2.03 (m, 1H), 1.89 (s, 3H), 1.74-1.62 (m, 1H), 1.61-1.51 (m, 1H), 1.50-1.40 (m, 1H), 1.30-1.20 (m, 1H); ES/MS m/z 382.5 [M+H]$^+$.

EXAMPLE 4

(R)-[5-(2-Methoxy-6-methyl-pyridin-3-yl)-2H-pyrazol-3-yl]-[6-(piperidin-3-yloxy)-pyrazin-2-yl]-amine hemioxalate salt

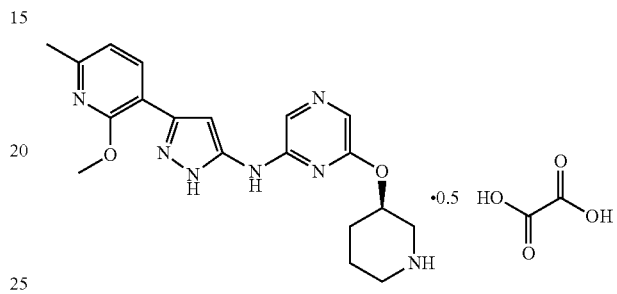

To a solution of (R)-[5-(2-methoxy-6-methyl-pyridin-3-yl)-2H-pyrazol-3-yl]-[6-(piperidin-3-yloxy)-pyrazin-2-yl]-amine (0.100 g, 0.26 mmol) in dichloromethane (10 mL) is added oxalic acid (0.012 mg, 0.13 mmol) dissolved in MeOH (0.1 mL) at 0° C. The reaction mixture is stirred for 60 min at room temperature and then the solvent evaporated to obtain a residue. The residue is triturated with diethyl ether (20 mL) followed by n-pentane (20 mL). The material is dried under high vacuum for 4 h to obtain the titled compound. Yield=0.095 g (77%). $^1$H NMR (400 MHz, DMSO-$d_6$) δ 9.77 (s, 1H), 8.07 (s, 1), 7.95 (d, J=7.6 Hz, 1H), 7.55 (s, 1H), 6.95 (d, J=7.6 Hz, 1H), 6.79 (s, 1H), 5.33-5.24 (m, 1H), 3.97 (s, 3H), 3.45-3.30 (m, 2H), 3.18-3.09 (m, 1H), 3.08-2.98 (m, 1H), 2.42 (s, 3H), 2.05-1.85 (m, 2H), 1.74-1.63 (m, 1-1.18-1.10 (m, 1H); ES/MS m/z 382.4 [M+H]$^+$.

EXAMPLE 5

(R)-[5-(2-Methoxy-6-methyl-pyridin-3-yl)-2H-pyrazol-3-yl]-[6-(piperidin-3-yloxy)-pyrazin-2-yl]-amine hemisuccinate salt

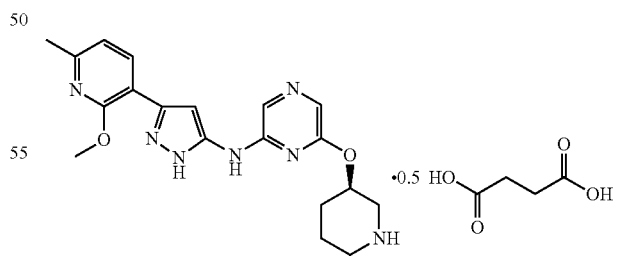

To a solution of (R)-[5-(2-methoxy-6-methyl-pyridin-3-yl)-2H-pyrazol-3-yl]-[6-(piperidin-3-yloxy)-pyrazin-2-yl]-amine (0.1 g, 0.26 mmol) in dichloromethane (10 mL) is added succinic acid (0.015 g, 0.13 mmol) dissolved in ethanol (1 mL, dissolved at 50° C.) at room temperature. The reaction mixture is stirred for 2 h at room temperature. The solvent is evaporated and the residue obtained is triturated with diethyl ether (20 mL) followed by n-pentane (20 mL). The material is dried under high vacuum for 8 h to obtain the title compound. Yield=0.102 g (78%). $^1$H NMR (400 MHz, DMSO-d$_6$) δ 12.4 (bs, 1H), 9.72 (s, 1H), 8.05-7.96 (m, 2H), 7.48 (s, 1H), 6.93 (d, J=7.6 Hz, 1H), 6.86 (s, 1H), 5.06-4.97 (m, 1H), 3.97 (s, 3H), 2.90-2.81 (m, 1H), 2.74-2.62 (m, 1H), 2.42 (s, 3H), 2.30 (s, 2H), 2.09-2.01 (m, 1H), 1.80-1.60 (m, 2H), 1.57-1.46 (m, 1H), 1.14-1.10 (m, 1H), 1.10-1.00 (m, 1H); ES/MS m/z 382.4 [M+H]$^+$.

EXAMPLE 6

(R)-[5-(2-Methoxy-6-methyl-pyridin-3-yl)-2H-pyrazol-3-yl]-[6-(piperidin-3-yloxy)-pyrazin-2-yl]-amine hydrate Suspend (R)-[5-(2-methoxy-6-methyl-pyridin-3-yl)-2H-pyrazol-3-yl]-[6-(piperidin-3-yloxy)-pyrazin-2-yl]-amine (52.1 mg; ES/MS m/z 382.2 [M+H]$^+$) in 5.95 water-ethanol mixture (10 mL) and slurry at ambient temperature for 48 hours. A white crystalline solid is recovered by vacuum filtration.

X-Ray powder diffraction (XRD) patterns of crystalline solids are obtained on a Bruker D4 Endeavor X-ray powder diffractometer, equipped with a CuKa source (λ=1.54060 Å) and a Vantec detector, operating at 35 kV and 50 mA. The sample is scanned between 4 and 40° in 2θ, with a step size of 0.009° in 2θ. The dry powder is packed on a quartz sample holder and a smooth surface is obtained using a glass slide. In the present case, a peak position variability of ±0.2 in 2θ takes into account potential variations without hindering the unequivocal identification of the indicated crystal form. Confirmation of a crystal form may be made based on any unique combination of distinguishing peaks (in units of 2θ), typically the more prominent peaks. The crystal form diffraction patterns, collected at ambient temperature and relative humidity, were adjusted based on NIST 675 standard peaks at 8.85 and 26.77 degrees 2-theta.

Thus, a sample crystalline form of the compound is characterized by an XRD pattern using CuKa radiation as having diffraction peaks (2-theta values) as described in Table 1 below, Specifically the pattern contains a peak at 5.17 in combination with one or more of the peaks selected from the group consisting of 15.73, 17.71 and 20.12 with a tolerance for the diffraction angles of 0.2 degrees.

TABLE 1

X-ray powder diffraction peaks of Example 6.

| Peak | Angle (2-Theta °) | Intensity (%) |
|---|---|---|
| 1 | 5.17 | 100.0 |
| 2 | 8.44 | 6.3 |
| 3 | 9.58 | 6.3 |
| 4 | 10.44 | 6.4 |
| 5 | 13.21 | 4.4 |
| 6 | 15.73 | 47.9 |
| 7 | 16.17 | 6.4 |
| 8 | 17.71 | 28.1 |
| 9 | 18.00 | 9.2 |
| 10 | 20.12 | 15.1 |
| 11 | 23.31 | 4.9 |
| 12 | 24.52 | 4.3 |
| 13 | 32.95 | 4.2 |

Chk1 Biochemical Assay

The effect of compounds on Chk1 biochemical activity can be determined using a CHK1/substrate peptide filter binding assay. In this assay, a synthetic peptide based on the amino acid sequence residues 206-225 of Cdc25, is used as a phospho-acceptor substrate for recombinant Chk1 protein kinase. Using γ-$^{33}$P-ATP as the phospho-donor substrate, Chk1 transfers the radioactive γ-$^{33}$phosphate group to the synthetic peptide. The reaction is measured by capturing the peptide substrate on a cation exchange paper filter plate and scintillation counting of emitted beta particles.

The kinase reactions (40 μL reaction volumes) are performed in 96-well V-bottom polystyrene plates. Reactions are initiated with the addition of Chk1 enzyme. Final reaction conditions are 67 mM HEPES sodium salt pH 7.4, 0.007% v/v) TRITON™ X-100, 2.7 mM DTT, 2.7 mM MgCl$_2$, 12 μM peptide substrate, 60 μM ATP disodium salt, 0.75 μCi γ-$^{33}$P-ATP, 0.75 nM active Chk1 enzyme, 4% (v/v) DMSO and serial dilution of the compound (1:3 serial dilution, starting at 20 μM, 10 points).

Following Chk1 enzyme addition, the reactions are incubated at room temperature for 90 min, and then terminated with the addition of 140 μL of phosphoric acid. The reaction mixture is transferred to the corresponding wells of a phosphocellulose cation exchange paper opaque filter plate to sit for 30 min. The filter plate is washed in a vacuum manifold with five washes of 200 of 0.5% phosphoric acid (v/v). The filter plate is dried overnight prior to the addition of 40 μL of Microscint™-20 to each well of the plate. After sitting for 4 h at room temperature, the radioactivity in the plate is measured using a MicroBeta Trilux microplate scintillation counter (Perkin Elmer).

For IC$_{50}$ determination, the percent inhibition for each concentration is calculated using the scintillation count ratio from controls run on each plate. The ten-point compound concentration data is subsequently fit to a four-parameter logistic equation using ActivityBase 4.0. Absolute IC$_{50}$ values are calculated from the resulting curve. Compounds of the invention are tested in this assay run substantially as above. For example, the compound of Example 1 is tested and found to have an IC$_{50}$, of <0.001 μM (n=6). Furthermore, the compound of Example 2 is tested and found to have an IC$_{30}$ of <0.001 μM (n=3). These results indicate that compounds within the scope of the present invention are potent inhibitors of Chk1.

Chk2 Biochemical Assay

The effect of compounds on Chk2 biochemical activity can be determined using a CHK2/substrate peptide filter binding assay. In this assay, a synthetic peptide based on the amino acid sequence residues 206-225 of Cdc25C, is used as a phospho-acceptor substrate for recombinant Chk2 protein kinase. Using γ-$^{33}$P-ATP as the phospho-donor substrate, Chk2 transfers the radioactive γ-$^{33}$phosphate group to the synthetic peptide. The reaction is measured by capturing the peptide substrate on a cation exchange paper filter plate and scintillation counting of emitted beta particles.

The kinase reactions (40 μL reaction volumes) are performed in 96-well V-bottom polystyrene plates. Reactions are initiated with the addition of Chk2 enzyme. Final reaction conditions are 67 mM HEPES sodium salt pH 7.4, 0.007% (v/v) TRITON™ X-100, 2.7 mM DTT, 2.7 mM MgCl$_2$, 12 μM peptide substrate, 60 μM ATP disodium salt, 0.75 μCi γ-$^{33}$P-ATP, 1.4 nM active Chk2 enzyme, 4% (v/v) DMSO and serial dilution of the compound (1:3 serial dilution, starting at 20 μM, 10 points).

Following Chk2 enzyme addition, the reactions are incubated at room temperature for 90 min, and then terminated with the addition of 140 μL of phosphoric acid. The reaction mixture is transferred to the corresponding wells of a phosphocellulose cation exchange paper opaque filter plate to sit for 30 min. The filter plate is washed in a vacuum manifold with five washes of 200 µL, of 0.5% phosphoric acid (v/v). The filter plate is dried overnight prior to the addition of 40 µL of Microscint™-20 to each well of the plate. After sitting for 4 h at room temperature, the radioactivity in the plate is measured using a MicroBeta Trilux microplate scintillation counter (Perkin Elmer).

For $IC_{50}$ determination, the percent inhibition for each concentration is calculated using the TR-FRET ratio from controls run on each plate. The ten-point compound concentration data is subsequently fit to a four-parameter logistic equation using ActivityBase 4.0. Absolute $IC_{50}$ values are calculated from the resulting curve. Compounds of the invention are tested in this assay run substantially as above. For example, the compound of Example 1 is tested and found to have an $IC_{50}$ of 0.011 µM (SE=0.002, n=6). Furthermore, the compound of Example 2 is tested and found to have an $IC_{50}$ of 0.012 µM (SE=0.008, n=3). These results indicate that compounds within the scope of the present invention are potent inhibitors of Chk2.

Chk1 Autophosphorylation Cell Based Assay

An inhibitor of Chk1 will prevent the kinase activity of the protein from phosphorylating substrates in cells in which the DNA damage response has been activated. An easily detectable substrate for Chk1 is an autophosphorylation site on Chk1 itself, serine 296. The following immunoblot assay can be used to measure the amount of phosphorylation of serine 296 on Chk1 and indirectly the activity level of the Chk1 protein kinase. HeLa cells are cultured in MEM w/Earle's Balanced Salt Solution with L-glutamine supplemented with 10% (v/v) heat inactivated fetal bovine serum, 1×MEM non-essential amino acids, 1× sodium pyruvate and $1 \times 10^5$ cells plated in 600 µL of MEM culture media per well of a 21 well cell culture plate. Cells are incubated for 24 h at 37° C., 5% $CO_2$ and 95%-400% humidity. Sixteen µL of a 4 µM stock of doxorubicin in culture media are added to each appropriate well to make a final concentration of 100 nM doxombicin. Plates are returned to the incubator for 24 additional hours prior to Chk1 inhibitor compound addition. Compounds are solubilized at 10 µM in 100% DMSO, then diluted to 2 mM in 40% (v/v) DMSO and then diluted to 100 µM with culture media plus 4% (v/v) DMSO. Subsequently, serial dilutions of the compounds (1:3) are prepared over a 100 µM to 0.005 µM range. Sixty-six µL of compound stock is added to the appropriate wells in the plate to produce a final DMSO concentration of 0.4% (v/v) and a final compound concentration range between 1 µM and 0.0005 µM. The plates are returned to the incubator for an additional 2 h and then removed for cell lysis and processing. The media is then removed from the plate, each well washed once with 0.5 mL of ice cold Dulbecco's Phosphate-Buffered Saline (DPBS), all liquid is removed, and the plate is placed on ice for the remainder of the procedure. To each well is added 75 µL of ice cold lysis buffer, consisting of Cell Extraction Buffer containing phosphatase inhibitor cocktail (Sigma, cat# P0044+P57251 and protease inhibitor cocktail tablets (Roche Diagnostics, cat#11836153001). After 10 min each well is scraped and the lysate transferred into a 1.5 mL polypropylene microcentrifuge tube on ice. Each lysate is sonicated for 45 sec with a plate cuphorn sonicator (Misonix) while suspended in a water/ice bath, Fifty µL of each sample is transferred into a 0.5 mL polypropylene microcentrufuge tube containing 25 µL of 4× Laemmli Sample Buffer, heated at 95° C. for 5 min and stored frozen at −80° C. The remaining lysate is used for determination of protein concentration (BCA protein assay kit, Thermo Scientific). Five µg of each cell lysate in sample buffer is applied to an E-Page 96 well gel and subjected to electrophoresis. Proteins are electrotransferred from the gel to Immobilon-P membrane PVDF (0.45 µm) according to procedures well understood in the art (Towbin al., PNAS (1979) 76(9), 4350-4), The membrane is rinsed briefly with 10 mM Tris/HCl pH 8.0, 150 mM NaCl and 0.05% (v/v) Tween 20 (TBST) and soaked for one hour at 25° C. in TBST/5% (v/v) reconstituted Carnation® instant milk. The membrane is washed four times with TBST for 5 min, then soaked at 4° C. for 24 h in TBST/5% (w/v) bovine serum albumin with an appropriate dilution of rabbit anti-phospho-Chk1 (serine 296). The membrane is washed 4× with TBST for 5 min at 25° C. and then soaked at 25° C. for 2 h TBST/5% milk containing an appropriate dilution of donkey anti-rabbit IgG conjugated to horseradish peroxidase (GE Healthcare, cat# NA9340) to detect autophosphorylated Chk1 protein. The membrane is washed again 4× with TBST for 5 min at 25° C. Antigen-antibody-reporter conjugates immobilized on the membrane are detected with the Super Signal Western Femto HRP-detection reagent using a FUJI LAS-4000 imaging system. Phospho-Chk1 (ser296) band intensities are calculated using "Total Lab" software (Nonlinear Dynamics). The percent inhibition of the doxorubicin induced Chk1 autophosphorylation is calculated by using the following formula: % inhibition=(sample-phospho-Chk1 band intensity-doxorubicin negative control-phospho-Chk1 band intensity)/(doxorubicin positive control-phospho-Chk1 band intensity-doxorubicin negative control-phospho-Chk1 band intensity)×100. Compounds of the invention are tested in this assay run substantially as above. The compound of Example 1 is tested in this assay and found to have an $EC_{50}$ of <0.001 µM (n=1). The compound of Example 3 is tested in this assay and found to have an $EC_{30}$ of <0.001 (n=1). These results indicate that compounds within the scope of the present invention are potent inhibitors of Chk1.

Doxorubicin-induced G2M Checkpoint Abrogation HeLa Cell-Based Acumen Assay

An inhibitor of Chk1 will disable the G2M DNA damage checkpoint in p53-minus tumor cells treated with the topoisomerase II inhibitor, doxorubicin. A measurement of G2M checkpoint abrogation is the phosphorylation of histone H3 on serine 10 that occurs after cells traverse the G2M checkpoint and enter mitosis. The following high content imaging assay can be used to measure the phosphorylation histone H3 in cells. HeLa cells are cultured in MEM Media supplemented with 10% (v/v) FBS and plated at 2000 cells per well in poly D-lysine coated clear bottom black plates, 100 µL volume per well. Plates are then incubated in a cell culture incubator for 18-24 h (37° C., 5% $CO_2$ and 95% relative humidity), Following the initial incubation, 20 µL of MEM Media plus 10% FBS containing 625 nM doxorubicin are added to the appropriate wells of the plates resulting in a final concentration of 125 nM. The plates are returned to the incubator for 24 h, sufficient to arrest the cells at the G2M checkpoint. The next day the cells are treated 1.0 with compounds. Compounds are solubilized at 10 nM in 100% DMSO and then diluted to a 10× stock starting at 50 µM in MEM plus 4% (v/v) DMSO. Subsequently, serial dilutions of the compounds (1:2) are prepared over a 50 µM to 0.39 µM range. Thirteen µL of compound stock is added to the appropriate wells in the plate to produce a final DMSO concentration of 0.4% and a final compound concentration range between 5 and 0.039 µM. The plates are returned to the incubator for an additional 7 h and then removed for fixation. Liquid is carefully removed from each well and 100 μL of PREFER™ fixative is added. Plates are retained at room temperature for 20 min, the fixative removed and the cells are then permeablized by the addition of 100 μL/well of 0.1% (v/v) Triton® X 100 in DPBS for 10 min. The solution is removed and the plate washed twice with 100 DPBS per well followed by the addition of 100 μL of DPBS containing 50 μg/mL Ribonuclease A (RNAase, from bovine pancreas) for one hour at room temperature. File RNAase solution is removed and the cells stained for the presence of histone H3 phosphorylated serine 10 (pHH3) by adding to each well 50 μL of RNAase solution containing a 1:500 dilution of rabbit anti-pHH3 (ser10) plus 1% (w/v) BSA. Plates are sealed and kept at 4° C. overnight. The primary antibody is removed by washing each plate twice with 100 μL DPBS per well and replaced with 50 μL of a 1:750 dilution of Alexa Fluor® 488 goat anti-rabbit IgG (H+L) 2 mg/mL) in DPBS plus 1% (w/v) BSA. Plates are kept for one hour at room temperature covered with aluminum foil to protect from light. The plates are again washed twice with 100 μL per well DPBS and replaced with 100 μL of 15 nM propidium iodide (1:100 dilution with PBS from the original solution). The plates are sealed with a black seal to protect the plates from light. Plates are incubated for 30 min to stain nuclei. Plates are scanned with ACUMEN EXPLORER™ Laser-scanning fluorescence microplate cytometers using 488 nm excitation (TTP LABTECH LTC) to measure pHH3 and DNA content including 2N, and 4N, The pHH3 positive cells are identified by mean intensity at 519 nm from Alexa 488. Total intensity at 655-705 nm from propidium iodide/DNA is used to identify individual cells and subpopulations in cell cycle (2N cells, 4N cells). The final readout for each population is determined by normalizing to the % of total cells producing a final assay output of % pHH3, % 2N, and % 4N. 100% activity is then determined by treating cells with the maximum concentration of an inhibitor control compound at 100 nM to determine the final % activity of each compound. 0% activity is based on no compound treatment. The Relative $EC_{50}$ is determined by using ACTIVITY BASE™, excel fit, curve fitting using a four parameter logistic fit, equation 205, to determine the % pHH3 relative to control max at 100%, Compounds of the invention are tested in this assay run substantially as above. The compound of Example 1 is tested and found to have an $EC_{50}$ of 0.029 μM (n=1). The compounds of Example 2 and Example 3 are tested and found to have $EC_{50}$ results of 0.033 μM (n=1) and 0.019 μM (n=1) respectively. These results indicate that compounds within the scope of the present invention will disable the G2M DNA damage checkpoint.

$EC_{tfs}$ (Two-Fold Sensitization) Assay

An inhibitor of Chk1 can potentiate the anti-proliferative activity of gemcitabine (or other cytotoxics) through abrogation of the intra-S phase checkpoint, resulting in sustained and increased DNA damage. The capacity for continued tumor cell proliferation after DNA damage can be analyzed by determining the ability of cells to replicate their DNA. This assay assesses the ability of cells to replicate their DNA after cells have had an opportunity to repair DNA damage. In this assay, cells are treated with a dilution series of gemcitabine, and then 22 h later with the compound of Example 3, After an additional 44 h, the relative cell number is assessed by a MTS (3-(4,5-dimethylthiazol-2-yl)-5-(3-carboxymethoxyphenyl)-2-(4-sulfophenyl)-2H-tetrazolium) dye reduction assay. The $EC_{tfs}$ parameter is a measure of the concentration of a Chk1 inhibitor necessary to reduce by half the (1190 concentration of gemcitabine, measured in this assay in the absence of Chk1 inhibition. HT-29 cells (obtained from ATCC), are grown in RPMI 1640 plus 10% (v/v) heat inactivated FBS, The cells are plated at $2.5 \times 10^3$ per well, in a volume of 100 μL on 96-well tissue culture plates and incubated for 24 h. Gemcitabine dilutions are prepared at 6× concentrations in McCoy's 5A medium (modified) (1×) and added to wells at 20 μper well. Gemcitabine dilutions were set up with the highest final concentration of gemcitabine being 1.0 μM and dilutions made by three-fold steps to 0.5 nM.

Chk1 Inhibitor is prepared by dilutions in DMSO to 4000× final concentration, and then diluted 666-fold into McCoy's medium to generate 6× stocks. Chk1 inhibitor dilutions proceed by 2.5-fold steps starting at 25 nM down to 0.3 nM. Twenty-two hours 1.0 after gemcitabine addition, Chk1, inhibitor is added in a volume of 24 μL to wells containing 120 μL of medium plus gemcitabine. Each gemcitabine dilution receives a single Chk1 inhibitor dilution. Control wells received DMSO, gemcitabine, or Chk1 inhibitor alone. Forty-four hours after addition of Chk1 inhibitor, 30 μL of CellTiter 96® $AQ_{ueous}$ assay reagent, is added to each well and held at room temperature for 1 hour and 45 minutes. Absorbance is read on a SpectraMax 250 (Molecular Devices) spectrophotometer at 490 nm. Data from the SpectraMax spectrophotometer are analyzed with GraphPad Prism 4.0. First, an averaged no cell control absorbance is subtracted from all other values in the matrix of data from each plate. Next, duplicate data points are averaged. Data are normalized for each Chk1 inhibitor concentration, with 0% cell number set as corrected $A_{490}=0$, and 100% cell number set as the 0 nM gemcitabine mean value. These results are then transformed. Gemcitabine concentrations are converted to log concentrations, and normalized cell number values are converted to percent inhibition (percent inhibition=1.00-normalized value). Transformed data are plotted, and a nonlinear regression is run to estimate an $IC_{50}$ value for gemcitabine at each Chk1 inhibitor concentration. The nonlinear regression is calculated allowing the slope to vary, and without constraints for the top or bottom of the dose-response curves. The $EC_{tfs}$ value is calculated as follows: $GI_{50}$ values for gemcitabine for each Chk1 inhibitor concentration are determined, plotted, and the concentration of Chk1 inhibitor necessary to decrease the gemcitabine alone $GI_{50}$ by two-fold is determined by interpolation.

Compounds within the scope of the invention are tested in this assay run substantially as above. For example, the compound of Example 3 is tested and found to have an $EC_{tfs}$ value of 1.0 nM (SE=0.1, n=3). Furthermore, 25 nM of the compound decreases the $EC_{50}$ of gemcitabine 7-fold from 22 nM to 3 nM in HT-29 colon carcinoma cells. Alone, 25 nM of the compound of Example 3 has little effect on the proliferation of HT-29 cells. These results indicate that compounds within the scope of the present invention effectively potentiate the anti-proliferative activity of gemcitabine low concentrations.

Gemcitabine $IC_{50}$ values obtained with treatment of various concentrations of Example 3

| [Example 3], nM | $IC_{50}$ (nM) |
|---|---|
| 0 | 22 |
| 0.256 | 23 |
| 0.64 | 19 |
| 1.60 | 14 |
| 4.0 | 10 |
| 10 | 4 |
| 25 | 3 |

Chk1 In Vivo Target Inhibition Assay

Calu-6 cells are cultured in growth media (MEM with Earle's Balanced Salt Solution with L-glutamine supplemented with 1.0% (v/v) heat inactivated EBS, 1×MEM non-essential amino acids, 1× sodium pyruvate) and expanded. Cells are harvested and washed twice with phosphate buffered saline and $1 \times 10^6$ cells in growth media (without serum) are mixed with equal volume of BD Matrigel™ matrix, then injected subcutaneously into the flank of pre-irradiated (4.5 Gy) nude mice (athymic nude). At day 15 after implant (tumor size=150-200 mm$^3$), gemcitabine formulated fresh in saline daily is administered to animals by intraperitoneal route at 150 mg/kg dose. Six hours later animals are orally administered Chk1 compound formulated in 0.2% Tween-80/0.5% methylcellulose pH adjusted to 6.8 by addition of dilute NaOH. Animals are sacrificed 2 h post Chk1 inhibitor dose, tumors harvested and immediately processed in ice cold Cell Extraction buffer containing phosphatase inhibitor cocktail (Sigma, cat# P0044+P5725) and protease inhibitor cocktail tablets (Roche Diagnostics, cat#11836153001) Tumors are processed in 1.5-2.0 mL of lysis buffer in an iced 15 mL polypropylene conical tube using a motorized tissue homogenizer set to high for 15 sec. With the sample kept on ice, the lysate is drawn four times through a 1 mL syringe with a 25 gauge needle. 0.35 mL of tumor lysate is transferred into a 1.5 mL polypropylene microcentrifuge tube containing 0.15 mL of 4× Laemmli sample buffer. Sample is then mixed and heated for 5 min at 95° C. and sonicated for 1 min using high power on a Misonix 3000 plate horn sonicator. Samples are then stored on ice, or stored at −80° C. for target inhibition assessment by western blot. Five μg of each tumor lysate in sample buffer is applied to E-Page 96 well gels and subjected to electrophoresis. Proteins are transferred to nitrocellulose BA83 Protran membrane (Whatman, Cat#10402405) according to procedures well understood in the art (Towbin et al., PNAS (1979) 76(9), 4350-4). The membrane is then processed to measure Chk1 protein autophosphorylated on serine 296. The membrane is rinsed briefly with water, then 10 mM Tris/HCl pH 8.0, 150 nM NaCl and 0.05% (v/v) Tween 20 (TBST) and soaked for one hour at 25° C. TBST/5% (w/v) reconstituted Carnation instant milk. The membrane is then washed four times with TBST for 5 min. The membrane is soaked at 4° C. for 16 h in TBST/5% (w/v) BSA in an appropriate dilution of rabbit-phospho-Chk1 anti-phospho-Chk1 (serine 296). Then the membrane is washed four times with TBST for 5 mM at 25° C. and then soaked at 25° C. for 2 h in TBST/5% milk containing an appropriate dilution of donkey anti-rabbit IgG conjugated to horseradish peroxidase to detect phospho-Chk1 (ser296). The membrane is washed again four times with TBST for 5 min at 25° C. Antigen-antibody-reporter conjugates immobilized on the membrane are detected with the Super Signal Western Femto HRP-detection reagent.

Signals are detected and captured using the FUJI LAS-4000 imaging system. Phospho-Chk1(ser296) band intensities are calculated using "Total Lab" software (Nonlinear Dynamics). The percent inhibition of the gemcitabine induced Chk1 autophosphorylation is calculated by using the following formula: % inhibition=(sample-phospho-Chk1 band—intensity average gemcitabine (Max) positive control-phospho-Chk1 band intensity)/(average negative control (Min)-phosphor-Chk1 band intensity—average gemcitabine (Max) positive control-phospho-Chk1 band intensity)×100.

Compounds within the scope of the invention are tested in this assay nm substantially as above. For example, the compound of Example 3 is tested and found to have a Target Modulatory Effective Dose 50 (TMED$_{50}$) for Chk1 autophosphorylation of 1.3 mg/kg (n=1). This result indicates that compounds within the scope of the present invention potently inhibit the activation of the Chk1 protein kinase in vivo.

Human Tumor Xenograft Models

The ability of Chk1 inhibitors to potentiate tumor killing by DNA damaging agents can be determined in vivo using the Calu-6 lung and HT-29 colon tumor xenograft efficacy models. Calu-6 lung cancer cells are cultured in growth media (MEM with Earle's Balanced Salt Solution with L-glutamine supplemented with 10% (v/v) heat inactivated FBS, 1×MEM non-essential amino acids, 1× sodium pyruvate) and HT-29 colon cancer cells (ATCC) are cultured in growth media, (McCoy's 5A medium supplemented with 10% FBS) and expanded.

Cells are harvested and washed twice with phosphate buffered saline and $5 \times 10^6$ cells (HT-29) or $1 \times 10^6$ a cells (Calu-6) in growth media (without serum) are mixed with equal volume of BD Matrigel™ matrix, then injected subcutaneously into the flank of nude mice (CD-1 nu/nu).

Subcutaneous Administration of Cal Inhibitor

At about day 16 after implant (150-200 min$^3$), gemcitabine is formulated fresh in saline daily and administered to animals by intraperitoneal route at 60 mg/kg dose. Twenty four hours later animals are administered the compound of Example 3, in 0.2% Tween-80/0.5% methylcellulose subcutaneously BID. After two days of rest, dosing is repeated for three additional cycles (Q4Dx4 with the compound of Example 3 offset+24 hours), Tumor growth inhibition (TGI) is calculated as the percent reduction in mean tumor size of a compound treated group from the mean tumor size of the vehicle-treated control group. Compounds within the scope of the invention are tested in this assay run substantially as above. For example, the compound of Example 3 dosed in combination with gemcitabine is found to demonstrate excellent dose dependent anti-tumor activity in both the HT-29 and Calu-6 tumor xenograft models, with up to a six-fold increase in tumor growth inhibition over gemcitabine alone. This result indicates that compounds within the scope of the present invention administered subcutaneously significantly increase the anti-tumor activity of gemcitabine in human tumor xenograft models.

HT29 Subcutaneous

| Treatment | % TGI at day 38 | p vs gem |
|---|---|---|
| Vehicle | 0 | ns |
| Gemcitabine 60 mpk | 11 | — |
| Example 3 40 mpk | 26 | ns |
| Gem/Ex 3 5 mpk | 47 | 0.0226 |
| Gem/Ex 3 10 mpk | 55 | 0.0024 |
| Gem/Ex 3 20 mpk | 58 | 0.0008 |
| Gem/Ex 3 40 mpk | 72 | <0.0001 | ns = not statistically significant

Calu 6 Subcutaneous

| Treatment | % TGI at day 47 | p vs gem |
|---|---|---|
| Vehicle | 0 | ns |
| Gem 60 mpk | −41 | — |
| Example 3 40 mpk | −19 | ns |
| Gem/Ex 3 5 mpk | 40 | 0.0049 |
| Gem/Ex 3 10 mpk | 32 | 0.0156 |

-continued

| Treatment | % TGI at day 47 | p vs gem |
|---|---|---|
| Gem/Ex 3 20 mpk | 68 | <0.0001 |
| Gem/Ex 3 40 mpk | 81 | <0.0001 | ns = not statistically significant

Oral Administration of Chk1 Inhibitor

At about day 16 after implant (150-200 mm$^3$), gemcitabine is formulated fresh in saline daily and administered to animals by intraperitoneal route at 40 mg/kg dose. Twenty four hours later animals are administered Chk1 compound, in 0.2% Tween-80/0.5% methylcellulose by the oral route MD. After three days of rest, dosing was repeated for three additional cycles (Q5Dx4 with the compound of Example 3 offset+24 hours). Tumor growth inhibition (TGI) is calculated as described in the previous paragraph. Compounds within the scope of the invention are tested in this assay run substantially as above. For example, the compound of Example 3 is dosed in combination with gemcitabine and found to demonstrate excellent dose dependent anti-tumor activity in both the HT-29 and Calu-6 tumor xenograft models, with up to a 2,9-fold increase in tumor growth inhibition over gemcitabine alone. This result indicates that compounds within the scope of the present invention administered orally significantly increase the anti-tumor activity of gemcitabine in human tumor xenograft models.

Calu6 Oral

| Treatment | % TGI at day 37 | p vs gem |
|---|---|---|
| Vehicle | 0 | 0.0171 |
| Gem 40 mpk | 32 | — |
| Example 3 30 mpk | 37 | ns |
| Gem/Ex 3 15 mpk | 48 | 0.0652 |
| Gem/Ex 3 30 mpk | 75 | <0.0001 | ns = not statistically significant

HT29 Oral

| Treatment | % TGI at day 50 | p vs gem |
|---|---|---|
| Vehicle | 0 | ns |
| Gem 40 mpk | 25 | — |
| Example 3 30 mpk | 39 | ns |
| Gem/Ex 3 15 mpk | 68 | <0.0001 |
| Gem/Ex 3 30 mpk | 73 | <0.0001 | ns = not statistically significant

We claim:

1. A compound which is (R)-[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof.

2. The compound according to claim 1 which is (R)-[5-(2-methoxy-6-methyl-pyridin-3-yl)-2H-pyrazol-3-yl]-[6-(piperidin-3-yloxy)-pyrazin-2-yl]-amine.

3. The compound according to claim 1 which is (R)-[5-(2-methoxy-6-methyl-pyridin-3-yl)-2H-pyrazol-3-yl]-[6-(piperidin-3-yloxy)-pyrazin-2-yl]-amine methane sulfonic acid salt.

4. The compound according to claim 1 which is (R)-[5-(2-methoxy-6-methyl-pyridin-3-yl)-2H-pyrazol-3-yl]-[6-(piperidin-3-yloxy)-pyrazin-2-yl]-amine acetic acid salt.

5. The compound according to claim 1 which is (R)-[5-(2-methoxy-6-methyl-pyridin-3-yl)-2H-pyrazol-3-yl]-[6-(piperidin-3-yloxy)-pyrazin-2-yl]-amine hemioxalate salt.

6. The compound according to claim 1 which is (R)-[5-(2-methoxy-6-methyl-pyridin-3-yl)-2H-pyrazol-3-yl]-[6-(piperidin-3-yloxy)-pyrazin-2-yl]-amine hemisuccinate salt.

7. A pharmaceutical composition comprising a compound which is (R)-[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof, and a pharmaceutically acceptable carrier, diluent, or excipient.

8. A method of treating a cancer wherein the cancer is selected from the group consisting of colon cancer, and lung cancer, comprising administering to a patient in need thereof an effective amount of a compound which is (R)-[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof.

9. A method of treating a cancer wherein the cancer is selected from the group consisting of colon cancer, and lung cancer, comprising administering to a patient in need thereof an effective amount of a compound which is (R)-[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof, and ionizing radiation.

10. A method of treating a cancer wherein the cancer is selected from the group consisting of colon cancer and lung cancer comprising administering to a patient in need thereof an effective amount of a compound which is (R)-[5-(2-methoxy-6-methyl-pyridin-3-yl)-2H-pyrazol-3-yl]-[6-(piperidin-3-yloxy)-pyrazin-2-yl]-amine, or a pharmaceutically acceptable salt thereof, and one or more chemotherapeutic agents wherein the one or more chemotherapeutic agents are selected from the group consisting of 5-fluorouracil, hydroxyurea, gemcitabine, methotrexate, pemetrexed, doxorubicin, etoposide, cisplatin, and Taxol®.

* * * * *